US010588563B2

(12) United States Patent
Yabe

(10) Patent No.: US 10,588,563 B2
(45) Date of Patent: Mar. 17, 2020

(54) LIVING-BODY-MOUNTED APPARATUS

(71) Applicant: Murata Manufacturing Co., Ltd., Nagaokakyo-shi, Kyoto-fu (JP)

(72) Inventor: Toru Yabe, Nagaokakyo (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 304 days.

(21) Appl. No.: 15/670,090

(22) Filed: Aug. 7, 2017

(65) Prior Publication Data

US 2017/0332957 A1    Nov. 23, 2017

Related U.S. Application Data

(63) Continuation of application No. PCT/JP2016/052958, filed on Feb. 1, 2016.

(30) Foreign Application Priority Data

Feb. 16, 2015    (JP) ................................. 2015-027270

(51) Int. Cl.
*A61B 5/00*    (2006.01)
*A61B 5/08*    (2006.01)
*A61B 5/11*    (2006.01)

(52) U.S. Cl.
CPC .......... *A61B 5/4205* (2013.01); *A61B 5/0803* (2013.01); *A61B 5/1123* (2013.01);
(Continued)

(58) Field of Classification Search
CPC ... A61B 5/4205; A61B 5/0803; A61B 5/1123; A61B 5/6822; A61B 5/6832
(Continued)

(56) References Cited

U.S. PATENT DOCUMENTS

2002/0107538 A1*    8/2002    Shibata .......... A61B 17/320068
                                                        606/169
2004/0082868 A1     4/2004    Campbell et al.
                              (Continued)

FOREIGN PATENT DOCUMENTS

JP    2005-304890 A    11/2005
JP    2008-301895 A    12/2008
                       (Continued)

OTHER PUBLICATIONS

Official Communication issued in International Patent Application No. PCT/JP2016/052958, dated May 10, 2016.

*Primary Examiner* — Daniel L Cerioni
(74) *Attorney, Agent, or Firm* — Keating & Bennett, LLP

(57) ABSTRACT

A living-body-mounted apparatus includes an apparatus main body, an electric-related attachment portion, and a flexible elongated member. The elongated member includes a living-body-side connector and an apparatus-main-body-side connector at a position midway through an electric cable thereof, and electrical conduction between the apparatus main body and the electric-related attachment portion is established while the connectors are connected. A condition of F1<F2 is satisfied, where F1 represents a minimum value of tensile load required for disconnection by moving the living-body-side connector and the apparatus-main-body-side connector relatively away from each other in a connected state and F2 represents a minimum value of tensile load required to detach the elongated member from the apparatus main body.

20 Claims, 8 Drawing Sheets

(52) U.S. Cl.
CPC .......... *A61B 5/6822* (2013.01); *A61B 5/6832* (2013.01); *A61B 2562/0204* (2013.01); *A61B 2562/0209* (2013.01); *A61B 2562/164* (2013.01); *A61B 2562/168* (2013.01); *A61B 2562/222* (2013.01); *A61B 2562/224* (2013.01); *A61B 2562/225* (2013.01); *A61B 2562/227* (2013.01)

(58) Field of Classification Search
USPC ........................................................ 600/587
See application file for complete search history.

(56) References Cited

U.S. PATENT DOCUMENTS

| | | | |
|---|---|---|---|
| 2008/0306373 A1 | 12/2008 | Kandori et al. | |
| 2009/0227907 A1* | 9/2009 | Kandori | A61B 5/11 600/593 |
| 2015/0165201 A1 | 6/2015 | Oku | |

FOREIGN PATENT DOCUMENTS

| | | | |
|---|---|---|---|
| JP | 2011-019925 A | 2/2011 | |
| JP | 2012-200300 A | 10/2012 | |
| JP | 2014-030540 A | 2/2014 | |
| WO | 2005/049129 A1 | 6/2005 | |
| WO | 2014/038390 A1 | 3/2014 | |

\* cited by examiner

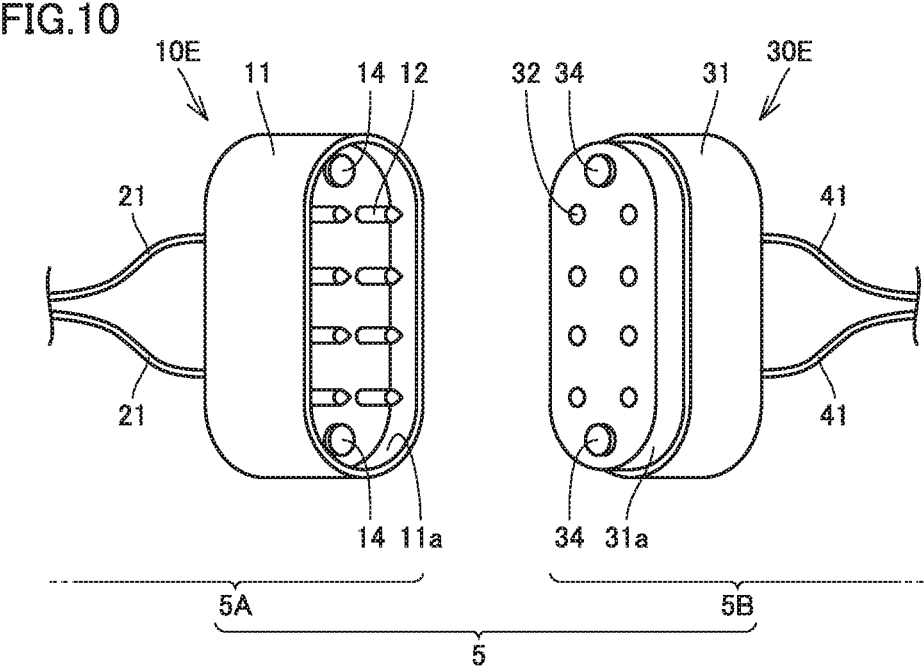

LIVING-BODY-MOUNTED APPARATUS

CROSS REFERENCE TO RELATED APPLICATIONS

This application claims the benefit of priority to Japanese Patent Application No. 2015-027270 filed on Feb. 16, 2015 and is a Continuation Application of PCT Application No. PCT/JP2016/052958 filed on Feb. 1, 2016. The entire contents of each application are hereby incorporated herein by reference.

BACKGROUND OF THE INVENTION

1. Field of the Invention

The present invention relates to a living-body-mounted apparatus including an electric cable which is a flexible elongated member connecting an apparatus main body and an electric-related attachment portion attached to any part of a living body to each other.

2. Description of the Related Art

Various living-body-mounted apparatuses have conventionally been known. Living-body-mounted apparatuses are represented, for example, by various biological information measurement apparatuses (e.g., a so-called medical monitor) for measuring biological information with a sensor, and the biological information measurement apparatuses include, for example, a swallowing function measurement apparatus, a sphygmograph, an electroencephalograph, and an electrocardiograph.

Among these apparatuses, the swallowing function measurement apparatus is an apparatus for determining whether or not one suffers from dysphagia or measuring a degree of dysphagia if any, and it has increasingly been put into practical use in recent years. In measuring swallowing functions, any of a motion of a neck portion in a swallowing action and a swallowing sound generated in a swallowing action, or both of them should be observed.

A technique to observe a motion of the neck portion in a swallowing action includes a technique to observe a motion with a potential sensor as a variation in a surface myopotential of the neck portion (see, for example, Japanese Patent Laying-Open No. 2005-304890) and a technique to observe a motion directly with an acceleration sensor, a pressure sensor, or a magnetic sensor (see, for example, Japanese Patent Laying-Open No. 2005-304890, Japanese Patent Laying-Open No. 2012-200300, and Japanese Patent Laying-Open No. 2008-301895). A method of observing swallowing sound generated in a swallowing action includes a technique to directly observe swallowing sound with a sound pressure sensor (what is called a microphone) (see, for example, Japanese Patent Laying-Open No. 2008-301895).

In any of these techniques, at least any of the various sensors described above should be attached to the neck portion or a portion around the same. Therefore, in the swallowing function measurement apparatus, in general, an electric-related attachment portion where a sensor is provided and an apparatus main body are separately constructed, and the electric-related attachment portion and the apparatus main body are connected to each other through an electric cable which is a flexible elongated member.

In a biological information measurement apparatus, an electric-related attachment portion should be attached to a living body in a stable manner for a prescribed period of time. In this case, even though a body motion of the living body occurs, the electric-related attachment portion should be prevented from being displaced in position or coming off. When a body motion of the living body occurs, the electric cable which is the flexible elongated member is pulled, which may result in toppling or falling of the apparatus main body and break of the biological information measurement apparatus.

Therefore, normally, the electric cable is often set to be relatively long so as to sag to some extent, and it is generally constructed to absorb motions of the living body in an extra portion thereof.

According to such a construction, however, for example, when a subject moves, due to the extra length of the electric cable, handling of the electric cable becomes troublesome.

Some biological information measurement apparatuses are constructed such that a pair of connectors are removably provided at a position midway through the electric cable and connection between a living body and an apparatus main body through the electric cable can temporarily be cut by detaching the connector as necessary while the electric-related attachment portion is attached to the living body. In this case, in order to prevent unintended detachment of the connector, normally, a pair of connectors which can firmly be connected to each other is used.

According to such a construction, however, attachment and detachment of the connector is often difficult, and handling of the connector, for example, by elderly people or children themselves is difficult.

Regardless of whether or not the connector as described above is provided, when a long electric cable is set, an extra portion of the electric cable may inadvertently be entangled with a living body. For example, in a biological information measurement apparatus of which electric-related attachment portion is attached to an upper body of a living body as in the swallowing function measurement apparatus described above, an extra portion of the electric cable may be entangled with a neck portion. In particular, when the biological information measurement apparatus is used while a subject is sleeping or unconscious, measures for avoiding entanglement of the extra portion of the electric cable with the neck portion due to a body motion of the living body caused by roll-over or a stroke should be taken.

Various problems described above are not limited to those in the biological information measurement apparatus, and are likely also in a living-body-mounted apparatus other than the biological information measurement apparatus. Solution of such problems has been needed but not satisfied.

SUMMARY OF THE INVENTION

Preferred embodiments of the present invention provide handling of a living-body-mounted apparatus including an electric cable which is a flexible elongated member to connect an apparatus main body and an electric-related attachment portion to each other, decrease the possibility of inadvertent entanglement of an electric cable with a living body, and prevent a living-body-mounted apparatus from breaking.

A living-body-mounted apparatus according to a preferred embodiment of the present invention includes an apparatus main body, an electric-related attachment portion attachable to any part of a living body, and a flexible elongated member connecting the electric-related attachment portion and the apparatus main body to each other. The elongated member includes a living-body-side cable including one end connected to the electric-related attachment portion, a living-body-side connector connected to the other end of the living-body-side cable, an apparatus-main-body-side cable including one end removably connected to the apparatus main body, and an apparatus-main-body-side connector connected to the other end of the apparatus-main-body-side cable. The living-body-side connector includes a first connection terminal electrically connected to the other end of the living-body-side cable, and the apparatus-main-body-side connector includes a second connection terminal electrically connected to the other end of the apparatus-main-body-side cable. The living-body-side connector and the apparatus-main-body-side connector are able to be in a connected state in which electrical conduction between the electric-related attachment portion and the apparatus main body is established as a result of contact between the first connection terminal and the second connection terminal owing to connection between the living-body-side connector and the apparatus-main-body-side connector and in a disconnected state in which electrical conduction between the electric-related attachment portion and the apparatus main body is cut off as a result of loss of contact between the first connection terminal and the second connection terminal owing to disconnection between the living-body-side connector and the apparatus-main-body-side connector. The living-body-side connector and the apparatus-main-body-side connector are provided with an engagement portion to maintain the connected state. The living-body-mounted apparatus according to a preferred embodiment of the present invention satisfies a condition of F1<F2, where F1 represents a minimum value of tensile load required to cut a connection between the living-body-side connector and the apparatus-main-body-side connector established by the engagement portion by moving the living-body-side connector and the apparatus-main-body-side connector relatively away from each other in the connected state and F2 represents a minimum value of tensile load required to detach the apparatus-main-body-side cable from the apparatus main body by moving the apparatus main body and the apparatus-main-body-side cable relatively away from each other while the apparatus-main-body-side cable is connected to the apparatus main body.

A living-body-mounted apparatus according to a preferred embodiment of the present invention includes an apparatus main body, an electric-related attachment portion attachable to any part of a living body, a fluid-related attachment portion attachable to any part of the living body, and a flexible elongated member connecting the electric-related attachment portion and the fluid-related attachment portion to the apparatus main body. The elongated member includes a living-body-side cable including one end connected to the electric-related attachment portion, a living-body-side tube including one end connected to the fluid-related attachment portion, a living-body-side connector connected to the other end of the living-body-side cable and the other end of the living-body-side tube, an apparatus-main-body-side cable including one end removably connected to the apparatus main body, an apparatus-main-body-side tube including one end removably connected to the apparatus main body, and an apparatus-main-body-side connector connected to the other end of the apparatus-main-body-side cable and the other end of the apparatus-main-body-side tube. The living-body-side connector includes a first connection terminal electrically connected to the other end of the living-body-side cable and a first connection port communicating with the other end of the living-body-side tube, and the apparatus-main-body-side connector includes a second connection terminal electrically connected to the other end of the apparatus-main-body-side cable and a second connection port communicating with the other end of the apparatus-main-body-side tube. The living-body-side connector and the apparatus-main-body-side connector can be in a connected state in which electrical conduction between the electric-related attachment portion and the apparatus main body is established as a result of contact between the first connection terminal and the second connection terminal owing to connection between the living-body-side connector and the apparatus-main-body-side connector and communication between the fluid-related attachment portion and the apparatus main body is established as a result of fitting between the first connection port and the second connection port and in a disconnected state in which electrical conduction between the electric-related attachment portion and the apparatus main body is cut off as a result of loss of contact between the first connection terminal and the second connection terminal owing to disconnection between the living-body-side connector and the apparatus-main-body-side connector and communication between the fluid-related attachment portion and the apparatus main body is cut off as a result of absence of fitting between the first connection port and the second connection port. The living-body-side connector and the apparatus-main-body-side connector are provided with an engagement portion to maintain the connected state. The living-body-mounted apparatus according to a preferred embodiment of the present invention satisfies a condition of F1<F2, where F1 represents a minimum value of tensile load required to cut a connection between the living-body-side connector and the apparatus-main-body-side connector established by the engagement portion by moving the living-body-side connector and the apparatus-main-body-side connector relatively away from each other in the connected state and F2 represents a minimum value of tensile load required to detach the apparatus-main-body-side cable and the apparatus-main-body-side tube from the apparatus main body by moving the apparatus-main-body-side cable and the apparatus-main-body-side tube relatively away from the apparatus main body while the apparatus-main-body-side cable and the apparatus-main-body-side tube are connected to the apparatus main body.

In a living-body-mounted apparatus according to a preferred embodiment of the present invention, preferably, a filter for filtration is removably assembled to at least one of the first connection port and the second connection port.

In a living-body-mounted apparatus according to a preferred embodiment of the present invention, preferably, F1 is equal to or lower than about 20 N, for example.

In a living-body-mounted apparatus according to a preferred embodiment of the present invention, preferably, L and La satisfy a condition of La≤L/2, where L represents a length along a direction of extension of the elongated member from an attachment end portion position to the apparatus main body, the attachment end portion position being a position closest to a side where the apparatus main body is located, in a portion of attachment of the living-body-mounted apparatus to the living body, and La represents a length along the direction of extension of the elongated member from the attachment end portion position to a position of connection between the living-body-side connector and the apparatus-main-body-side connector.

In a living-body-mounted apparatus according to a preferred embodiment of the present invention, the electric-related attachment portion may be attachable to any part of an upper body of a human body, and in this case, La preferably further satisfies a condition of about 30 cm≤La≤about 90 cm, for example.

In a living-body-mounted apparatus according to a preferred embodiment of the present invention, the engagement portion may include a magnet.

In a living-body-mounted apparatus according to a preferred embodiment of the present invention, the engagement portion may include a pressure-sensitive adhesive.

In a living-body-mounted apparatus according to a preferred embodiment of the present invention, the engagement portion may include a locking tab provided in one of the living-body-side connector and the apparatus-main-body-side connector and a locked portion provided in the other of the living-body-side connector and the apparatus-main-body-side connector and locked by the locking tab.

In a living-body-mounted apparatus according to a preferred embodiment of the present invention, preferably, at least one of the first connection terminal and the second connection terminal includes a contact probe.

In a living-body-mounted apparatus according to a preferred embodiment of the present invention, the engagement portion may include a conductive pressure-sensitive adhesive, and in this case, preferably, at least one of the first connection terminal and the second connection terminal includes the conductive pressure-sensitive adhesive.

A living-body-mounted apparatus according to a preferred embodiment of the present invention may be a biological information measurement apparatus that measures biological information. In this case, the electric-related attachment portion includes a sensor which converts biological information into an electric signal.

A living-body-mounted apparatus according to a preferred embodiment of the present invention may be a swallowing function measurement apparatus that measures a swallowing function. In this case, the electric-related attachment portion may include a piezoelectric film sensor attachable to a neck portion of the living body.

According to a preferred embodiment of the present invention, handling of a living-body-mounted apparatus including an electric cable which is a flexible elongated member to connect an apparatus main body and an electric-related attachment portion to each other is facilitated, a possibility of inadvertent entanglement of an electric cable with a living body is lessened, and a living-body-mounted apparatus is prevented from breaking.

The above and other elements, features, steps, characteristics and advantages of the present invention will become more apparent from the following detailed description of the preferred embodiments with reference to the attached drawings.

BRIEF DESCRIPTION OF THE DRAWINGS

FIG. 10 is a schematic diagram showing a construction of a living-body-side connector and an apparatus-main-body-side connector shown in FIG. 9.

DETAILED DESCRIPTION OF THE PREFERRED EMBODIMENTS

Figure 1:
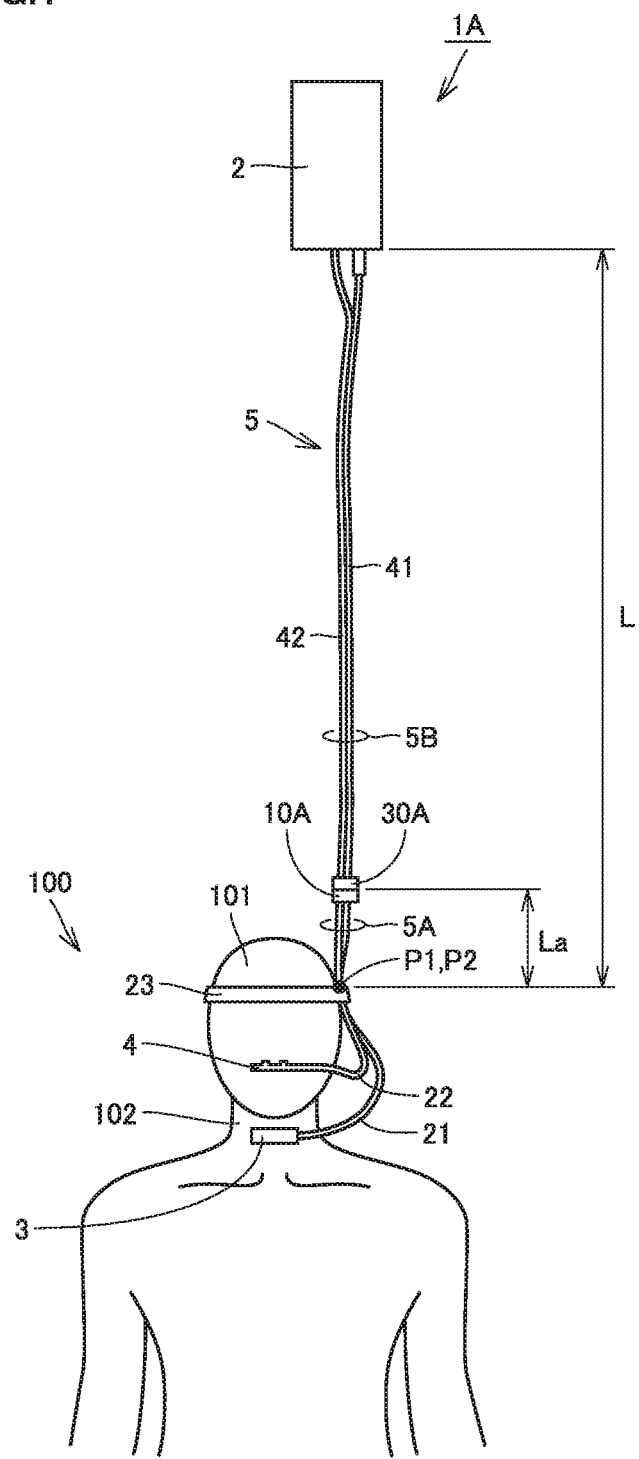
FIG. 1 is a schematic diagram showing a manner of use of a swallowing function measurement apparatus in a first preferred embodiment of the present invention.

Preferred embodiments of the present invention will be described below in detail with reference to the drawings. In the preferred embodiments described below, a swallowing function measurement apparatus representing one of biological information measurement apparatuses will be described by way of example as a living-body-mounted apparatus to which the present invention is applied. In the preferred embodiments described below, the same or common elements in the drawings have the same reference characters allotted and description thereof will not be repeated.

First Preferred Embodiment

FIG. 1 is a schematic diagram showing a manner of use of a swallowing function measurement apparatus in a first preferred embodiment of the present invention. A schematic construction of a swallowing function measurement apparatus 1A in the present preferred embodiment will initially be described with reference to FIG. 1.

A swallowing function measurement apparatus 1A in the present preferred embodiment is constructed to observe a motion of a neck portion and swallowing sound in a swallowing action of a subject with a piezoelectric film sensor attached to the neck portion and to observe a respiration action of the subject with a pressure sensor through a cannula attached to a nasal cavity. In the swallowing function measurement apparatus 1A thus constructed, analysis is conducted with a motion of the neck portion and the swallowing sound as well as the respiration action obtained as biological information being associated with one another and the swallowing function of the subject is able to be more appropriately be measured.

As shown in FIG. 1, the swallowing function measurement apparatus 1A mainly includes an apparatus main body 2, a sensor attachment portion 3 as an electric-related attachment portion, a cannula attachment portion 4 as a fluid-related attachment portion, and a connection portion 5 as a flexible elongated member.

A sensor attachment portion 3 includes a piezoelectric film sensor, and it is attached to a neck portion 102 of a subject 100, for example, with a pressure-sensitive adhesive applied to one surface thereof or a medical tape. The piezoelectric film sensor converts externally applied vibration into a voltage signal as an electric signal owing to a piezoelectric effect, and obtains a motion of neck portion 102 and swallowing sound in a swallowing action of subject 100 as biological information based on characteristics thereof.

Cannula attachment portion 4 includes a bifurcated cannula which can be inserted in the nasal cavity, and it is attached to a head portion 101 of subject 100, for example, with a medical tape. The cannula includes, for example, of a tube made of a resin, and provided with a hole communicating to the outside at a tip end portion of a bifurcation.

Connection portion 5 is divided into a living-body-side connection portion 5A located on a side of subject 100 and an apparatus-main-body-side connection portion 5B located on a side of apparatus main body 2. Living-body-side connection portion 5A includes a living-body-side connector 10A, a living-body-side cable 21, a living-body-side tube 22, and a fixing belt 23, and apparatus-main-body-side connection portion 5B includes an apparatus-main-body-side connector 30A, an apparatus-main-body-side cable 41, and an apparatus-main-body-side tube 42.

Living-body-side connector 10A and apparatus-main-body-side connector 30A can be connected to each other, and one of them is in a shape of a socket and the other of them is in a shape of a plug corresponding to the shape of the socket. In the present preferred embodiment, living-body-side connector 10A is in the shape of the socket and apparatus-main-body-side connector 30A is in the shape of the plug (see FIG. 2).

Living-body-side cable 21 and apparatus-main-body-side cable 41 include an electric cable in which a signal line including a conductive material is covered with an insulating coating material. Though each of living-body-side cable 21 and apparatus-main-body-side cable 41 preferably includes a composite wire in which a plurality of signal lines are provided, it may be made up of a bundle of non-composite lines in which only a single signal line is provided.

Living-body-side tube 22 and apparatus-main-body-side tube 42 both include a tube made of a resin. Each of living-body-side tube 22 and apparatus-main-body-side tube 42 is provided with one flow path along a direction of extension thereof.

Living-body-side cable 21 includes one end in the direction of extension thereof connected to sensor attachment portion 3 and the other end in the direction of extension thereof connected to living-body-side connector 10A. Living-body-side tube 22 includes one end in the direction of extension thereof connected to cannula attachment portion 4 and the other end in the direction of extension thereof connected to living-body-side connector 10A.

Though living-body-side cable 21 and living-body-side tube 22 are preferably bundled except for opposing end portions thereof from a point of view of handleability, they do not necessarily have to be constructed as such and they may be provided independently of each other.

Fixing belt 23 described above is provided at a prescribed position of living-body-side cable 21 and living-body-side tube 22. Fixing belt 23 fixes living-body-side cable 21 and living-body-side tube 22 to head portion 101 of subject 100, and includes, for example, a member made of a stretchable fabric.

A position of placement of fixing belt 23 on living-body-side cable 21 and living-body-side tube 22 is preferably set at a position where, in an attached state, both of a portion of living-body-side cable 21 connected to sensor attachment portion 3 closer to one end and a portion of living-body-side tube 22 connected to cannula attachment portion 4 closer to one end are relaxed to some extent. With such setting, even when connection portion 5 is pulled, the application of an external force to sensor attachment portion 3 and cannula attachment portion 4 is able to be lessened and a state of attachment of these portions to a living body is able to be maintained in a stable manner.

Fixing belt 23 does not necessarily have to be provided in living-body-side cable 21 and living-body-side tube 22 as described above, and living-body-side cable 21 and living-body-side tube 22 may be constructed separately. In this case, fixing belt 23 should only be attached to head portion 101 such that appropriate positions of living-body-side cable 21 and living-body-side tube 22 are fixed to head portion 101 of subject 100.

Apparatus-main-body-side cable 41 includes one end in the direction of extension thereof removably connected to apparatus main body 2 and the other end in the direction of extension thereof connected to apparatus-main-body-side connector 30A. Apparatus-main-body-side tube 42 includes one end in the direction of extension thereof removably connected to apparatus main body 2 and the other end in the direction of extension thereof connected to apparatus-main-body-side connector 30A.

Though apparatus-main-body-side cable 41 and apparatus-main-body-side tube 42 are preferably bundled except for opposing end portions thereof from a point of view of handleability, they do not necessarily have to be constructed as such and they may be provided independently of each other.

Apparatus main body 2 mainly includes a not-shown pressure sensor and a not-shown processing circuit, and it is connected to sensor attachment portion 3 and cannula attachment portion 4 with connection portion 5 described above being interposed.

The pressure sensor is placed to communicate with apparatus-main-body-side tube 42 connected to apparatus main body 2. Thus, variation in pressure which occurs in the vicinity of the hole provided in the cannula described above with a respiration action of subject 100 propagates to the pressure sensor through the cannula, living-body-side tube 22, and apparatus-main-body-side tube 42. Therefore, the pressure sensor converts such variation in pressure into an electric signal and the respiration action of subject 100 is able to be obtained as biological information.

The processing circuit obtains a motion of neck portion 102 and swallowing sound as well as a respiration action of subject 100 as biological information by accepting inputs of electric signals detected by the piezoelectric film sensor and the pressure sensor described above, and measures a swallowing action of subject 100 by conducting analysis with the obtained pieces of biological information being associated with one another. The electric signals detected by the piezoelectric film sensor are transmitted to apparatus main body 2 through living-body-side cable 21 and apparatus-main-body-side cable 41 described above.

A result of measurement by the processing circuit is stored in a not-shown storage provided in apparatus main body 2. The result of measurement is shown on a not-shown display provided in apparatus main body 2 as a not-shown operation portion provided in apparatus main body 2 is operated. The result of measurement may be transmitted through various interfaces to a terminal provided outside swallowing function measurement apparatus 1A.

Figure 2:
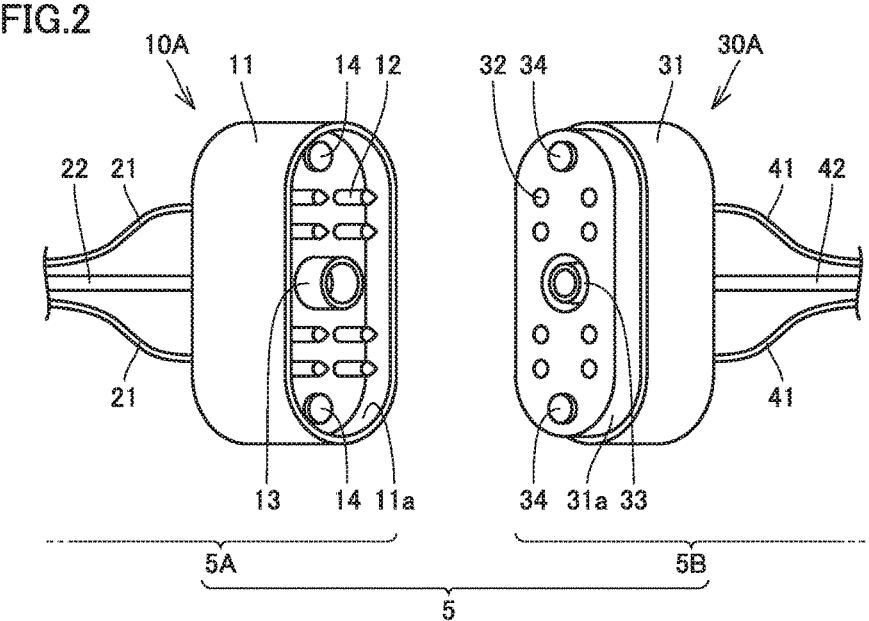
FIG. 2 is a schematic diagram showing a construction of a living-body-side connector and an apparatus-main-body-side connector shown in FIG. 1.
Figure 3A:
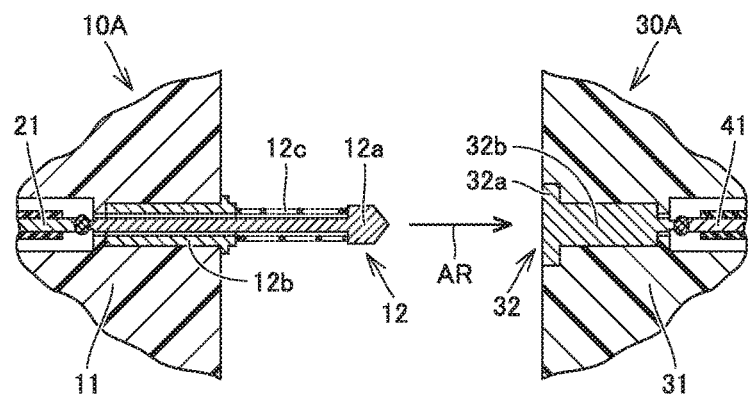
FIGS. 3A and 3B are schematic cross-sectional views showing a connection structure of first and second connection terminals provided in the living-body-side connector and the apparatus-main-body-side connector shown in FIG. 2.
Figure 3B:
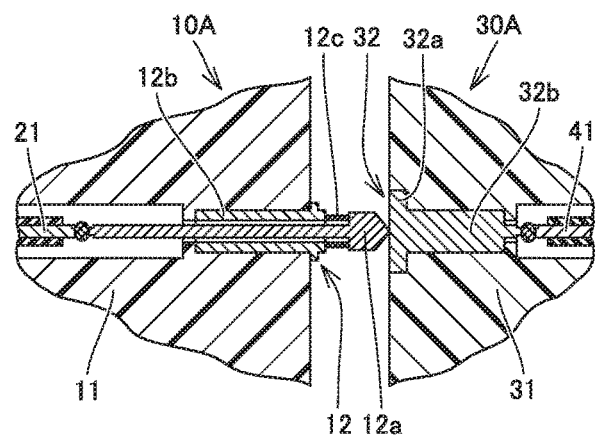
Figure 4A:
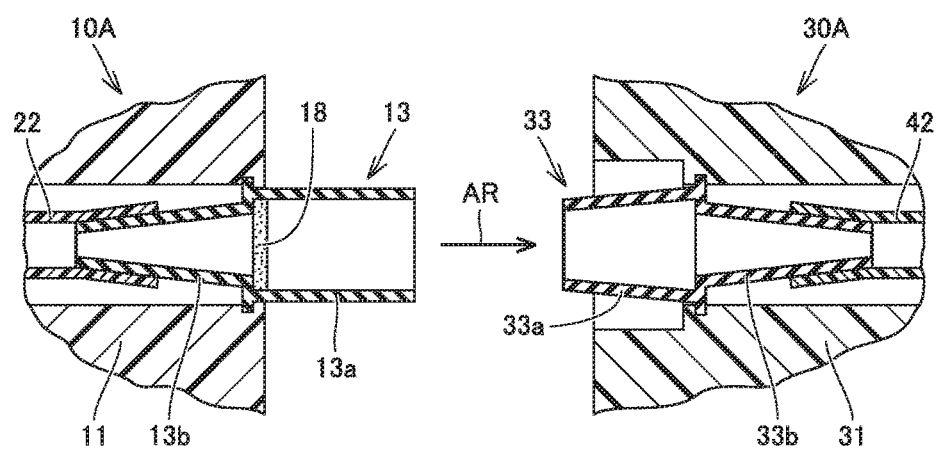
FIGS. 4A and 4B are schematic cross-sectional views showing a connection structure of first and second connection ports provided in the living-body-side connector and the apparatus-main-body-side connector shown in FIG. 2.
Figure 4B:
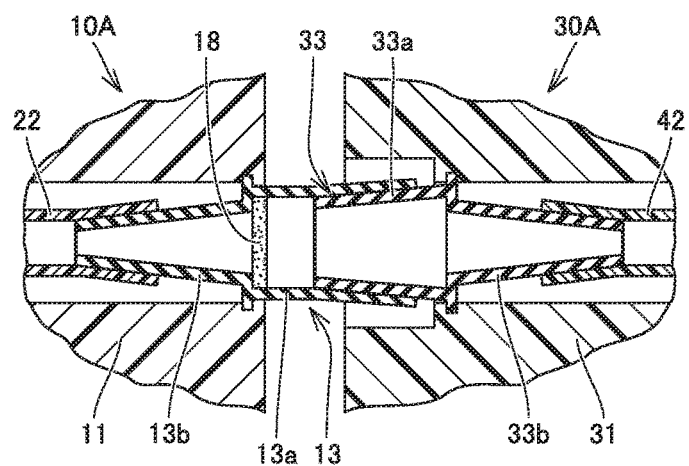

FIG. 2 is a schematic diagram showing a construction of the living-body-side connector and the apparatus-main-body-side connector shown in FIG. 1. FIGS. 3A and 3B are schematic cross-sectional views showing a connection structure of the first and second connection terminals provided in the living-body-side connector and the apparatus-main-body-side connector shown in FIG. 2, and FIGS. 4A and 4B are schematic cross-sectional views showing a connection structure of the first and second connection ports provided in the living-body-side connector and the apparatus-main-body-side connector shown in FIG. 2. FIGS. 3A and 4A show a disconnected state of the living-body-side connector and the apparatus-main-body-side connector and FIGS. 3B and 4B show a connected state of the living-body-side connector and the apparatus-main-body-side connector. A construction of living-body-side connector 10A and apparatus-main-body-side connector 30A provided in swallowing function measurement apparatus 1A in the present preferred embodiment and a connection structure thereof will be described below with reference to FIGS. 2 to 4B.

As shown in FIG. 2, living-body-side connector 10A includes a connector main body 11 in which a recess 11a is provided in a surface different from a surface from which living-body-side cable 21 and living-body-side tube 22 are pulled out, so that the socket shape described above is formed. A bottom surface of recess 11a in living-body-side connector 10A is provided with a plurality of first connection terminals 12, one first connection port 13, and a pair of magnets 14. A portion of each first connection terminal 12 is located to protrude like a pin from the bottom surface of recess 11a, and a portion of first connection port 13 is located to protrude like a nozzle from the bottom surface of recess 11a. Each of the pair of magnets 14 is located to protrude from the bottom surface of recess 11a and fixed, for example, as being adhered to connector main body 11.

As shown in FIGS. 2, 3A, and 3B, first connection terminal 12 is held by connector main body 11 such that a portion thereof is located in connector main body 11. In a portion of first connection terminal 12 located in connector main body 11, the other end of living-body-side cable 21 pulled into connector main body 11 (more strictly, a signal line in a portion located at the other end) is connected, for example, by soldering or screwing of a nut so that first connection terminal 12 is electrically connected to the other end of living-body-side cable 21.

As shown in FIGS. 3A and 3B, in the present preferred embodiment, first connection terminal 12 includes a contact probe. More specifically, first connection terminal 12 includes a rod provided with a contact element 12a at a tip end, a sleeve 12b in which the rod is inserted, and a spring 12c interposed between a tip end of sleeve 12b and a rear end of contact element 12a. Sleeve 12b is fixed to connector main body 11 and living-body-side cable 21 is connected to the rear end of the rod. The rod is thus movable along an axial direction thereof, and contact element 12a is retractable toward connector main body 11 with movement of the rod while contact element 12a is elastically biased by spring 12c.

As shown in FIGS. 2, 4A, and 4B, first connection port 13 is held by connector main body 11 such that a portion thereof is located in connector main body 11. The other end of living-body-side tube 22 pulled into connector main body 11 is connected to a portion of first connection port 13 located in connector main body 11. First connection port 13 thus communicates with the other end of living-body-side tube 22.

As shown in FIGS. 4A and 4B, in the present preferred embodiment, first connection port 13 includes a substantially cylindrical pipe joint. More specifically, first connection port 13 includes a tip-end-side nozzle portion 13a provided in a portion closer to a tip end portion located outside connector main body 11 and a rear-end-side nozzle portion 13b provided in a portion closer to a rear end portion located in connector main body 11. Rear-end-side nozzle portion 13b is in such a tapered shape that a diameter thereof decreases toward the rear end portion, and first connection port 13 and living-body-side tube 22 are fitted to each other as the other end of living-body-side tube 22 is externally attached to rear-end-side nozzle portion 13b.

As shown in FIG. 2, apparatus-main-body-side connector 30A includes connector main body 31 in which a projection 31a is provided on a surface different from a surface from which apparatus-main-body-side cable 41 and apparatus-main-body-side tube 42 are pulled out, so that it is in the plug shape described above. A top surface of projection 31a of apparatus-main-body-side connector 30A is provided with a plurality of second connection terminals 32, one second connection port 33, and a pair of magnets 34. A portion of each second connection terminal 32 is located as being exposed at the top surface of projection 31a and second connection port 33 is located such that a portion thereof protrudes like a nozzle from a bottom surface in a depression provided in the top surface of projection 31a while the portion is accommodated in the depression. A portion of each of the pair of magnets 34 is located to protrude from the top surface of projection 31a, and fixed, for example, by being adhered to connector main body 31.

As shown in FIGS. 2,3A, and 3B, second connection terminal 32 is held by connector main body 31 as being located in connector main body 31. The other end of apparatus-main-body-side cable 41 pulled into connector main body 31 (more strictly, a signal line in a portion located at the other end) is connected to a portion of second connection terminal 32 located in connector main body 31, for example, by soldering or screwing of a nut so that second connection terminal 32 is electrically connected to the other end of apparatus-main-body-side cable 41.

As shown in FIGS. 3A and 3B, in the present preferred embodiment, second connection terminal 32 includes a contact portion 32a including a planar exposed surface and a base portion 32b located in the rear of contact portion 32a. Base portion 32b is fixed to connector main body 31 and apparatus-main-body-side cable 41 is connected to a rear end of base portion 32b.

As shown in FIGS. 2, 4A, and 4B, second connection port 33 is held by connector main body 31 such that a portion thereof is located in connector main body 31. The other end of apparatus-main-body-side tube 42 pulled into connector main body 31 is connected to a portion of second connection port 33 located in connector main body 31 so that second connection port 33 communicates to the other end of apparatus-main-body-side tube 42.

As shown in FIGS. 4A and 4B, in the present preferred embodiment, second connection port 33 includes a substantially cylindrical pipe joint. More specifically, second connection port 33 includes a tip-end-side nozzle portion 33a provided in a portion closer to a tip end portion located outside connector main body 31 and a rear-end-side nozzle portion 33b provided in a portion closer to a rear end portion located in connector main body 31. Tip-end-side nozzle portion 33a is in such a tapered shape that a diameter thereof decreases toward the tip end portion. Rear-end-side nozzle portion 33b is in such a tapered shape that a diameter thereof decreases toward the rear end portion and second connection port 33 and apparatus-main-body-side tube 42 are fitted to each other as the other end of apparatus-main-body-side tube 42 is externally attached to rear-end-side nozzle portion 33b.

As shown in FIG. 2, recess 11a provided in living-body-side connector 10A and projection 31a provided in apparatus-main-body-side connector 30A are constructed to be fitted to each other. Each of the plurality of first connection terminals 12 and each of the plurality of second connection terminals 32, first connection port 13 and second connection port 33, and each of the pair of magnets 14 and each of the pair of magnets 34 are provided at corresponding positions in living-body-side connector 10A and apparatus-main-body-side connector 30A.

Therefore, as shown in FIGS. 3A and 4A, living-body-side connector 10A and apparatus-main-body-side connector 30A are able to be connected to each other by bringing living-body-side connector 10A and apparatus-main-body-side connector 30A relatively closer to each other (that is, bringing living-body-side connector 10A closer toward apparatus-main-body-side connector 30A along a direction, for example, shown with an arrow AR shown in the figures) while a state that recess 11a in living-body-side connector 10A and projection 31a in apparatus-main-body-side connector 30A face each other is maintained.

As shown in FIG. 3B, contact element 12a of first connection terminal 12 comes in contact with contact portion 32a of second connection terminal 32 so that the rod of first connection terminal 12 retracts toward connector main body 11 of living-body-side connector 10A. With retraction of the rod, spring 12c is compressed. Based on this elastic biasing force (that is, resilience), contact element 12a is elastically pressed to be in contact with contact portion 32a and a contact pressure between first connection terminal 12 and second connection terminal 32 is ensured.

As shown in FIG. 4B, tip-end-side nozzle portion 13a of first connection port 13 is externally attached to tip-end-side nozzle portion 33a of second connection port 33, so that first connection port 13 and living-body-side tube 22 are fitted to each other. As described above, with tip-end-side nozzle portion 33a of second connection port 33 being in the tapered shape, tip-end-side nozzle portion 13a of first connection port 13 elastically deforms to increase in diameter so that an inner circumferential surface of tip-end-side nozzle portion 13a of first connection port 13 and an outer circumferential surface of tip-end-side nozzle portion 33a of second connection port 33 come in intimate contact with each other and hermeticity in that portion is ensured.

As set forth above, in a connected state in which living-body-side connector 10A and apparatus-main-body-side connector 30A are connected to each other, each of the plurality of first connection terminals 12 and each of the plurality of second connection terminals 32 come in contact with each other so that electrical conduction between sensor attachment portion 3 and apparatus main body 2 is established. First connection port 13 and second connection port 33 are fitted to each other so that communication between cannula attachment portion 4 and apparatus main body 2 is established.

As shown in FIGS. 4A and 4B, in the present preferred embodiment, a filter 18 for filtration is removably assembled to the inside of tip-end-side nozzle portion 13a of first connection port 13. Filter 18 is a member that catches moisture or dust contained in breath. By thus providing filter 18 in tip-end-side nozzle portion 13a of first connection port 13, introduction of moisture or dust contained in breath into apparatus main body 2 is able to be prevented in the connected state in which communication between cannula attachment portion 4 and apparatus main body 2 is established described above, and failure of swallowing function measurement apparatus 1A is prevented.

By removably providing filter 18 in a portion of fitting between first connection port 13 and second connection port 33 as above, replacement or maintenance thereof is facilitated and convenience is improved. Filter 18 does not necessarily have to be assembled to the inside of tip-end-side nozzle portion 13a of first connection port 13 and may be assembled to the inside of tip-end-side nozzle portion 33a of second connection port 33.

In a disconnected state in which living-body-side connector 10A and apparatus-main-body-side connector 30A are disconnected from each other, each of the plurality of first connection terminals 12 is not in contact with each of the plurality of second connection terminals 32 so that electrical conduction between sensor attachment portion 3 and apparatus main body 2 is cut off. In addition, as first connection port 13 and second connection port 33 are not fitted to each other, communication between cannula attachment portion 4 and apparatus main body 2 is cut off.

The pair of magnets 14 and the pair of magnets 34 described above correspond to an engagement portion to maintain the connected state in which living-body-side connector 10A and apparatus-main-body-side connector 30A are connected to each other. Therefore, magnetic attraction force generated between the pair of magnets 14 and the pair of magnets 34 determines holding force of living-body-side connector 10A and apparatus-main-body-side connector 30A in the connected state.

In addition to magnetic attraction force of the pair of magnets 14 and the pair of magnets 34 described above, a force of fitting between recess 11a provided in living-body-side connector 10A and projection 31a provided in apparatus-main-body-side connector 30A and a force of fitting between tip-end-side nozzle portion 13a of first connection port 13 and tip-end-side nozzle portion 33a of second connection port 33 may be factors to determine holding force of living-body-side connector 10A and apparatus-main-body-side connector 30A in the connected state. By setting magnetic attraction force described above to be greater than force of fitting, a holding force of living-body-side connector 10A and apparatus-main-body-side connector 30A in the connected state is able to be determined by magnetic attraction force.

Swallowing function measurement apparatus 1A in the present preferred embodiment satisfies a condition of F1<F2 where F1 represents a minimum value of tensile load required to disconnect living-body-side connector 10A and apparatus-main-body-side connector 30A from each other against magnetic attraction force of the pair of magnets 14 and the pair of magnets 34 by moving living-body-side connector 10A and apparatus-main-body-side connector 30A relatively away from each other in the connected state and F2 represents a minimum value of tensile load required to detach apparatus-main-body-side cable 41 and apparatus-main-body-side tube 42 from apparatus main body 2 by moving apparatus-main-body-side cable 41 and apparatus-main-body-side tube 42 relatively away from apparatus main body 2 while apparatus-main-body-side cable 41 and apparatus-main-body-side tube 42 are connected to apparatus main body 2.

According to such a construction, when some external force is applied to swallowing function measurement apparatus 1A at the time of measurement, living-body-side connector 10A and apparatus-main-body-side connector 30A are disconnected from each other before connection portion 5 is detached from apparatus main body 2. Therefore, a possibility of inadvertent entanglement of the extra portion of connection portion 5 with the living body is lessened.

In swallowing function measurement apparatus 1A in the present preferred embodiment, a minimum value F1 of tensile load required to disconnect living-body-side connector 10A and apparatus-main-body-side connector 30A from each other is set to about 20 N or lower, for example. A minimum value F1 of tensile load may be set to about 15 N or lower or about 10 N or lower, for example.

By thus constructing living-body-side connector 10A and apparatus-main-body-side connector 30A such that they can be disconnected from each other with relatively small force, attachment and detachment of living-body-side connector 10A and apparatus-main-body-side connector 30A are facilitated. Therefore, for example, elderly people or children themselves can handle the connector, which contributes to convenience.

By constructing living-body-side connector 10A and apparatus-main-body-side connector 30A such that they are disconnected from each other with relatively small force as described above, possibility of inadvertent entanglement of the extra portion of connection portion 5 set to relatively be longer with the living body is further lessened. Since living-body-side connector 10A and apparatus-main-body-side connector 30A are disconnected from each other in a relatively early stage of a body motion of subject 100 in the attached state, possibility of inadvertent entanglement of the extra portion of connection portion 5 with the living body is further lessened.

In particular, since both of sensor attachment portion 3 and cannula attachment portion 4 should be attached to neck portion 102 or head portion 101 which are in an upper body of subject 100 in swallowing function measurement apparatus 1A described above, without any measures, the extra portion of connection portion 5 may be entangled with neck portion 102. By adopting the construction described above, living-body-side connector 10A and apparatus-main-body-side connector 30A are disconnected from each other in a relatively early stage of a body motion in the living body, and therefore the possibility of entanglement of connection portion 5 with neck portion 102 is significantly lessened. The effect is particularly noticeably exhibited in use of swallowing function measurement apparatus 1A while subject 100 is sleeping or is unconscious.

In order to further ensure the effect, referring to FIG. 1, L and La preferably satisfy a condition of La≤L/2, where L represents a length along a direction of extension of connection portion 5 from attachment end portion positions P1 and P2 to apparatus main body 2, attachment end portion positions P1 and P2 being positions closest to a side where apparatus main body 2 is located, in a portion of attachment of swallowing function measurement apparatus 1A to subject 100, and La represents a length along the direction of extension of connection portion 5 from attachment end portion positions P1 and P2 to a position of connection between living-body-side connector 10A and apparatus-main-body-side cable 30A (in the present preferred embodiment, since fixing belt 23 described above is provided at a position midway through living-body-side cable 21 and living-body-side tube 22, a position where fixing belt 23 fixes living-body-side cable 21 to subject 100 (a left temporal portion) corresponds to an electric-related attachment end portion position P1 and a position where fixing belt 23 fixes living-body-side tube 22 to subject 100 (similarly, the left temporal portion) corresponds to a fluid-related attachment end portion position P2).

According to such a construction, while living-body-side connector 10A and apparatus-main-body-side connector 30A are disconnected from each other, a length (that is, La) of connection portion 5 in a portion of attachment to subject 100 is able to be set to at most half the entire length (that is, L) of connection portion 5 and the possibility of entanglement of connection portion 5 with neck portion 102 is able to be significantly lessened.

When La satisfies a condition of about 30 cm≤La≤about 90 cm, a length of connection portion 5 in a portion of attachment to subject 100 is able to be sufficiently short while living-body-side connector 10A and apparatus-main-body-side connector 30A are disconnected from each other, and therefore the possibility of entanglement of connection portion 5 with neck portion 102 can further reliably be lessened. L is preferably set approximately to about 100 cm≤L≤about 200 cm from a point of view of usability, for example.

Additionally, by constructing living-body-side connector 10A and apparatus-main-body-side connector 30A such that they can be disconnected from each other with relatively small force as described above, apparatus main body 2 is able to be prevented from breaking. Since living-body-side connector 10A and apparatus-main-body-side connector 30A are disconnected from each other in a relatively early stage of a body motion of subject 100 in the attached state, apparatus main body 2 is able to be prevented from toppling or falling as connection portion 5 is pulled and hence swallowing function measurement apparatus 1A is prevented from breaking.

As described above, with swallowing function measurement apparatus 1A in the present preferred embodiment, handling thereof is facilitated, possibility of inadvertent entanglement of the electric cable with the living body is able to be lessened, and swallowing function measurement apparatus 1A is able to be prevented from breaking.

Since a plurality of electric cables and tubes are connected to one set of connectors in swallowing function measurement apparatus 1A in the present preferred embodiment, the plurality of electric cables and tubes are able to collectively be attached and detached. Handleability is improved also in this sense. By adopting such a construction, connection again is also able to be made in a one-touch operation. Handleability is improved also in that sense and measurement is able to immediately be resumed.

A layout of the plurality of first connection terminals 12, first connection port 13, and a set of magnets 14 arranged on a connection surface of living-body-side connector 10A and a layout of a plurality of second connection terminals 32, second connection port 33, and a set of magnets 34 arranged on a connection surface of apparatus-main-body-side connector 30A are preferably in line symmetry or rotation symmetry on the connection surface. By adopting such a layout, living-body-side connector 10A and apparatus-main-body-side connector 30A are able to be prevented from being disconnected from each other with force smaller than necessary. When a minimum value of tensile load required to disconnect living-body-side connector 10A and apparatus-main-body-side connector 30A from each other is able to appropriately be managed, however, the layout does not necessarily have to be in line symmetry or rotation symmetry.

Though an example in which a magnet as an engagement portion is provided in both of living-body-side connector 10A and apparatus-main-body-side connector 30A has been described above by way of example, a magnet may be provided in only one of living-body-side connector 10A and apparatus-main-body-side connector 30A and a magnetic body which is magnetically attracted by the magnet may be provided in the other.

Figure 5:
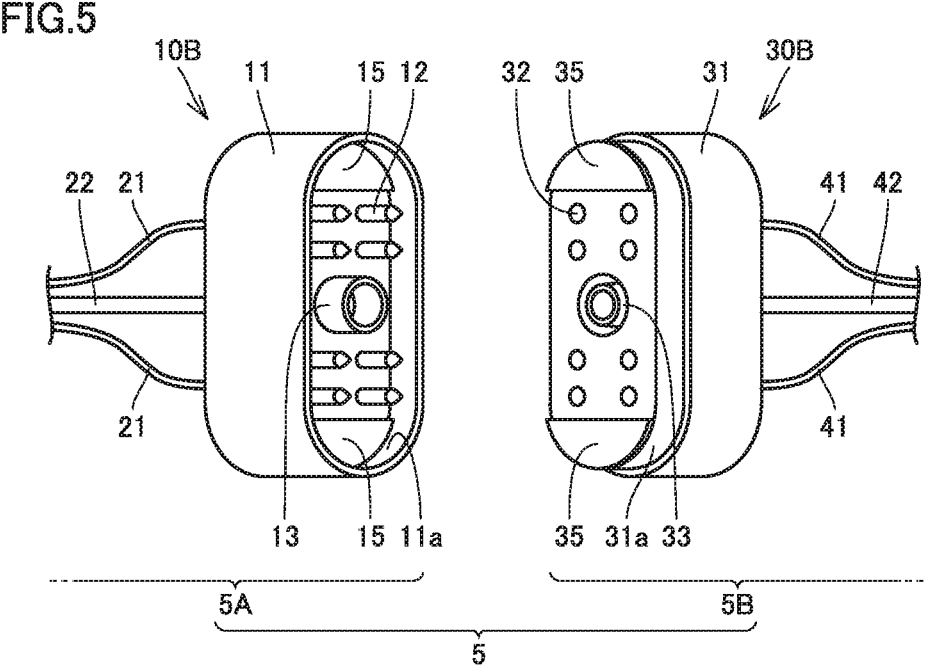
FIG. 5 is a schematic diagram showing a construction of a living-body-side connector and an apparatus-main-body-side connector according to a first modification of a preferred embodiment of the present invention.

FIG. 5 is a schematic diagram showing a construction of a living-body-side connector and an apparatus-main-body-side connector according to a first modification based on the first preferred embodiment described above. A construction of a living-body-side connector 10B and an apparatus-main-body-side connector 30B according to the first modification will be described below with reference to FIG. 5.

As shown in FIG. 5, living-body-side connector 10B and apparatus-main-body-side connector 30B according to the first modification are different from living-body-side connector 10A and apparatus-main-body-side connector 30A in the first preferred embodiment described above only in construction of the engagement portion. Specifically, a set of pressure-sensitive adhesive layers 15 as the engagement portion is provided in living-body-side connector 10B and a set of pressure-sensitive adhesive layers 35 as the engagement portion is provided in apparatus-main-body-side connector 30B. Pressure-sensitive adhesive layers 15 and 35 are stuck to a connection surface of living-body-side connector 10B and a connection surface of apparatus-main-body-side connector 30B, for example, with adhesiveness thereof, respectively.

According to such a construction, an adhesive force generated between the set of pressure-sensitive adhesive layers 15 and the set of pressure-sensitive adhesive layers 35 determines holding force of living-body-side connector 10B and apparatus-main-body-side connector 30B in the connected state.

In this case as well, by satisfying such a condition that minimum value F1 of tensile load required to disconnect living-body-side connector 10B and apparatus-main-body-side connector 30B from each other against adhesive force of the set of pressure-sensitive adhesive layers 15 and the set of pressure-sensitive adhesive layers 35 by moving living-body-side connector 10B and apparatus-main-body-side connector 30B relatively away from each other in the connected state is smaller than minimum value F2 of tensile load required to detach apparatus-main-body-side cable 41 and apparatus-main-body-side tube 42 from apparatus main body 2 by moving apparatus-main-body-side cable 41 and apparatus-main-body-side tube 42 relatively away from apparatus main body 2 while apparatus-main-body-side cable 41 and apparatus-main-body-side tube 42 are connected to apparatus main body 2 (that is, F1<F2) and additionally by setting minimum value F1 of tensile load required to disconnect living-body-side connector 10B and apparatus-main-body-side connector 30B from each other to 20 [N] or lower, an effect similar to the effect described in the first preferred embodiment above is obtained.

Though an example in which a pressure-sensitive adhesive layer is provided in both of living-body-side connector 10B and apparatus-main-body-side connector 30B has been described above by way of example, a pressure-sensitive adhesive layer may be provided in only one of living-body-side connector 10A and apparatus-main-body-side connector 30A.

Figure 6:
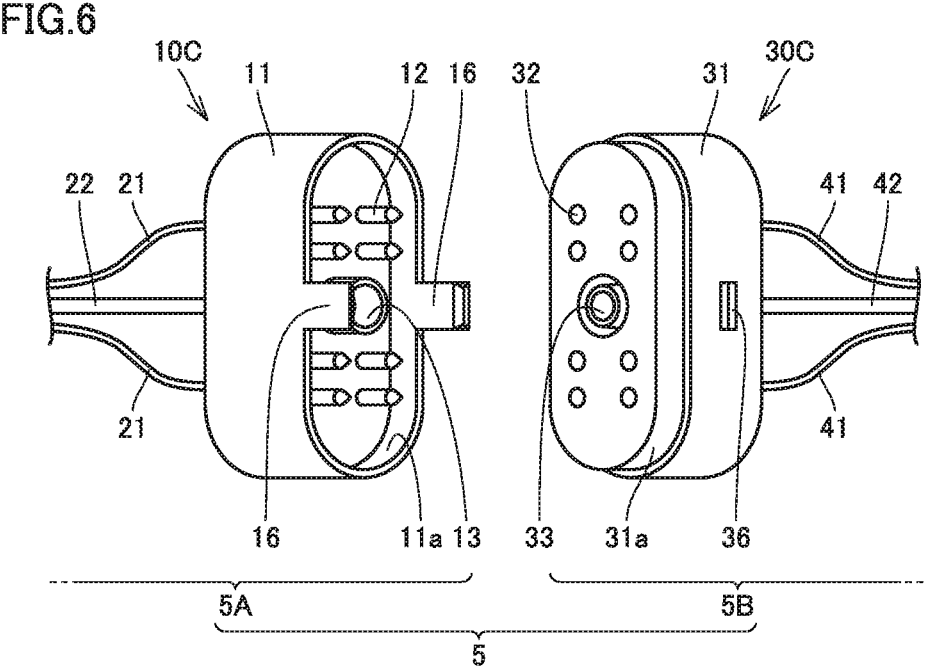
FIG. 6 is a schematic diagram showing a construction of a living-body-side connector and an apparatus-main-body-side connector according to a second modification of a preferred embodiment of the present invention.

FIG. 6 is a schematic diagram showing a construction of a living-body-side connector and an apparatus-main-body-side connector according to a second modification based on the first preferred embodiment described above. A construction of a living-body-side connector 10C and an apparatus-main-body-side connector 30C according to the second modification will be described below with reference to FIG. 6.

As shown in FIG. 6, living-body-side connector 10C and apparatus-main-body-side connector 30C according to the second modification are different from living-body-side connector 10A and apparatus-main-body-side connector 30A in the first preferred embodiment described above only in construction of the engagement portion. Specifically, a set of locking tabs 16 as the engagement portion is provided in living-body-side connector 10C and a set of recessed locked portions 36 (in the figure, only one of them is seen) as the engagement portion is provided in apparatus-main-body-side connector 30C. Locking tab 16 and locked portion 36 are both made up of a portion of connector main bodies 11 and 31.

Each of the set of locking tabs 16 is constructed to be locked to a corresponding locked portion of the set of locked portion 36 in the attached state. According to such a construction, engagement force generated between the set of locking tabs 16 and the set of locked portions 36 determines holding force of living-body-side connector 10C and apparatus-main-body-side connector 30C in the connected state.

In this case as well, by satisfying such a condition that minimum value F1 of tensile load required to disconnect living-body-side connector 10C and apparatus-main-body-side connector 30C from each other against engagement force of the set of locking tabs 16 and the set of locked portion 36 by moving living-body-side connector 10C and apparatus-main-body-side connector 30C relatively away from each other in the connected state is smaller than minimum value F2 of tensile load required to detach apparatus-main-body-side cable 41 and apparatus-main-body-side tube 42 from apparatus main body 2 by moving apparatus-main-body-side cable 41 and apparatus-main-body-side tube 42 relatively away from apparatus main body 2 while apparatus-main-body-side cable 41 and apparatus-main-body-side tube 42 are connected to apparatus main body 2 (that is, F1<F2) and additionally by setting minimum value F1 of tensile load required to disconnect living-body-side connector 10C and apparatus-main-body-side connector 30C from each other to about 20 N or lower, an effect similar to the effect described in the first preferred embodiment above is able to be obtained.

Though an example in which a set of locking tabs is provided in living-body-side connector 10C and a set of locked portions is provided in apparatus-main-body-side connector 30C has been described above by way of example, a set of locking tabs may be provided in apparatus-main-body-side connector 30C and a set of locked portions may be provided in living-body-side connector 10C.

Though an example in which a locking tab and a locked portion are provided independently of first connection terminal 12, second connection terminal 32, first connection port 13, and second connection port 33 has been exemplified above, the locking tab and the locked portion may also define and function as first connection terminal 12 and second connection terminal 32 or as first connection port 13 and second connection port 33.

Figure 7:
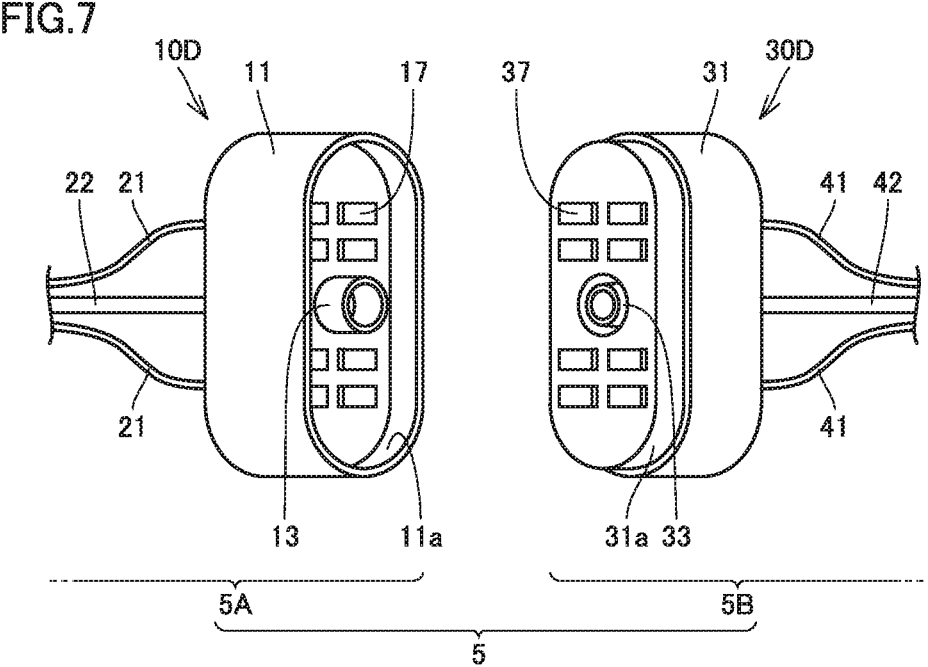
FIG. 7 is a schematic diagram showing a construction of a living-body-side connector and an apparatus-main-body-side connector according to a third modification of a preferred embodiment of the present invention.

FIG. 7 is a schematic diagram showing a construction of a living-body-side connector and an apparatus-main-body-side connector according to a third modification based on the first preferred embodiment described above. A construction of a living-body-side connector 10D and an apparatus-main-body-side connector 30D according to the third modification will be described below with reference to FIG. 7.

As shown in FIG. 7, living-body-side connector 10D and apparatus-main-body-side connector 30D according to the third modification are different from living-body-side connector 10A and apparatus-main-body-side connector 30A in the first preferred embodiment described above only in construction of the first and second connection terminal and the engagement portion. Specifically, a plurality of conductive pressure-sensitive adhesive layers 17 as the engagement portion are provided in living-body-side connector 10D and a plurality of conductive pressure-sensitive adhesive layers 37 as the engagement portion are provided in apparatus-main-body-side connector 30D.

Conductive pressure-sensitive adhesive layer 17 is stuck to a not-shown electrode provided in a connection surface of living-body-side connector 10D with its adhesiveness so as to cover the electrode, so that the first connection terminal includes the electrode and conductive pressure-sensitive adhesive layer 17. Conductive pressure-sensitive adhesive layer 37 is stuck to a not-shown electrode provided in a connection surface of apparatus-main-body-side connector 30D with its adhesiveness so as to cover the electrode, so that the second connection terminal includes the electrode and conductive pressure-sensitive adhesive layer 37.

According to such a construction, conductive pressure-sensitive adhesive layers 17 and 37 also define and function as the first and second connection terminals and the engagement portion, and adhesive force generated between the plurality of conductive pressure-sensitive adhesive layers 17 and the plurality of conductive pressure-sensitive adhesive layers 37 determines holding force of living-body-side connector 10D and apparatus-main-body-side connector 30D in the connected state.

In this case as well, by satisfying such a condition that minimum value F1 of tensile load required to disconnect living-body-side connector 10D and apparatus-main-body-side connector 30D from each other against adhesive force of the plurality of conductive pressure-sensitive adhesive layers 17 and the plurality of conductive pressure-sensitive adhesive layers 37 by moving living-body-side connector 10D and apparatus-main-body-side connector 30D relatively away from each other in the connected state is smaller than minimum value F2 of tensile load required to detach apparatus-main-body-side cable 41 and apparatus-main-body-side tube 42 from apparatus main body 2 by moving apparatus-main-body-side cable 41 and apparatus-main-body-side tube 42 relatively away from apparatus main body 2 while apparatus-main-body-side cable 41 and apparatus-main-body-side tube 42 are connected to apparatus main body 2 (that is, F1<F2) and additionally by setting minimum value F1 of tensile load required to disconnect living-body-side connector 10D and apparatus-main-body-side connector 30D from each other to about 20 N or lower, an effect similar to the effect described in the first preferred embodiment above is obtained.

Though an example in which a conductive pressure-sensitive adhesive layer is provided in both of living-body-side connector 10D and apparatus-main-body-side connector 30D has been described above by way of example, a conductive pressure-sensitive adhesive layer may be provided in only one of living-body-side connector 10D and apparatus-main-body-side connector 30D and an electrode may be exposed in the other.

Second Preferred Embodiment

Figure 8:
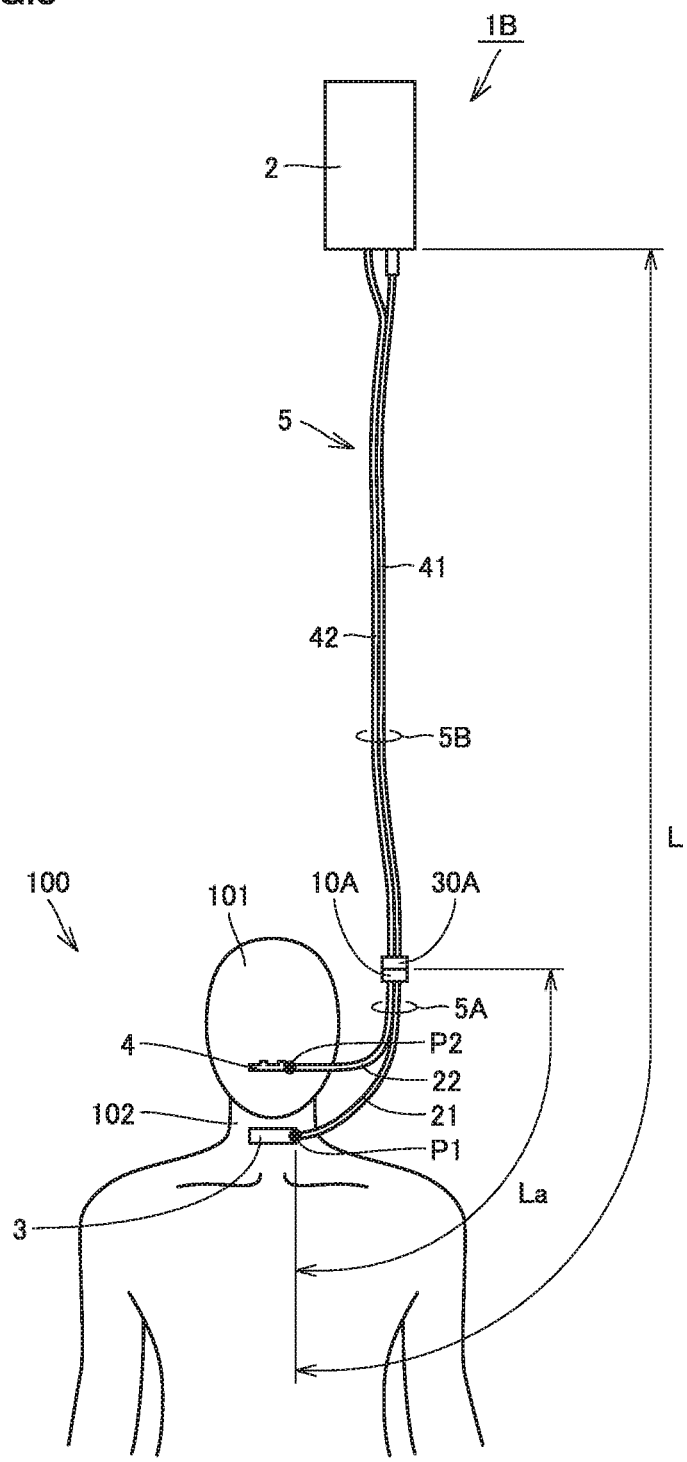
FIG. 8 is a schematic diagram showing a manner of use of a swallowing function measurement apparatus in a second preferred embodiment of the present invention.

FIG. 8 is a schematic diagram showing a manner of use of a swallowing function measurement apparatus in a second preferred embodiment of the present invention. A swallowing function measurement apparatus 1B in the present preferred embodiment will be described below with reference to FIG. 8.

As shown in FIG. 8, swallowing function measurement apparatus 1B in the present preferred embodiment is different from swallowing function measurement apparatus 1A in the first preferred embodiment described above only in that fixing belt 23 (see FIG. 1) is not provided in living-body-side cable 21 and living-body-side tube 22 which are a part of connection portion 5.

According also to such a construction, by satisfying such a condition that minimum value F1 of tensile load required to disconnect living-body-side connector 10A and apparatus-main-body-side connector 30A from each other by moving living-body-side connector 10A and apparatus-main-body-side connector 30A relatively away from each other in the connected state is smaller than minimum value F2 of tensile load required to detach apparatus-main-body-side cable 41 and apparatus-main-body-side tube 42 from apparatus main body 2 by moving apparatus-main-body-side cable 41 and apparatus-main-body-side tube 42 relatively away from apparatus main body 2 while apparatus-main-body-side cable 41 and apparatus-main-body-side tube 42 are connected to apparatus main body 2 (that is, F1<F2) and additionally by setting minimum value F1 of tensile load required to disconnect living-body-side connector 10A and apparatus-main-body-side connector 30A from each other to about 20 N or lower, an effect similar to the effect described in the first preferred embodiment above is obtained.

In the present preferred embodiment, electric-related attachment end portion position P1 which is a portion of sensor attachment portion 3 fixed to neck portion 102 of subject 100 and fluid-related attachment end portion position P2 which is a portion of cannula attachment portion 4 fixed to head portion 101 of subject 100 are candidates for an attachment end portion position which is a position closest to a side where apparatus main body 2 is located, in a portion of attachment of swallowing function measurement apparatus 1B to subject 100. In this case, based on comparison between a length from electric-related attachment end portion position P1 to a position of connection between living-body-side connector 10A and apparatus-main-body-side connector 30A along a direction of extension of living-body-side cable 21 and a length from fluid-related attachment end portion position P2 to a position of connection between living-body-side connector 10A and apparatus-main-body-side connector 30A along a direction of extension of living-body-side tube 22, a shorter length of them should only be determined as the attachment end portion position (FIG. 8 shows an example in which electric-related attachment end portion position P1 is determined as the attachment end portion position).

L and La preferably satisfy a condition of $La \leq L/2$ where L represents a length from the attachment end portion position to apparatus main body 2 along the direction of extension of connection portion 5 and La represents a length from the attachment end portion position to a position of connection between living-body-side connector 10A and apparatus-main-body-side connector 30A along the direction of extension of connection portion 5. According to such a construction, the possibility of entanglement of connection portion 5 with neck portion 102 is significantly reduced.

When La satisfies a condition of about 30 cm≤La≤about 90 cm, a length of connection portion 5 in a portion of attachment to subject 100 is able to be sufficiently short while living-body-side connector 10A and apparatus-main-body-side connector 30A are disconnected from each other, and therefore the possibility of entanglement of connection portion 5 with neck portion 102 is reliably further reduced.

Third Preferred Embodiment

Figure 9:
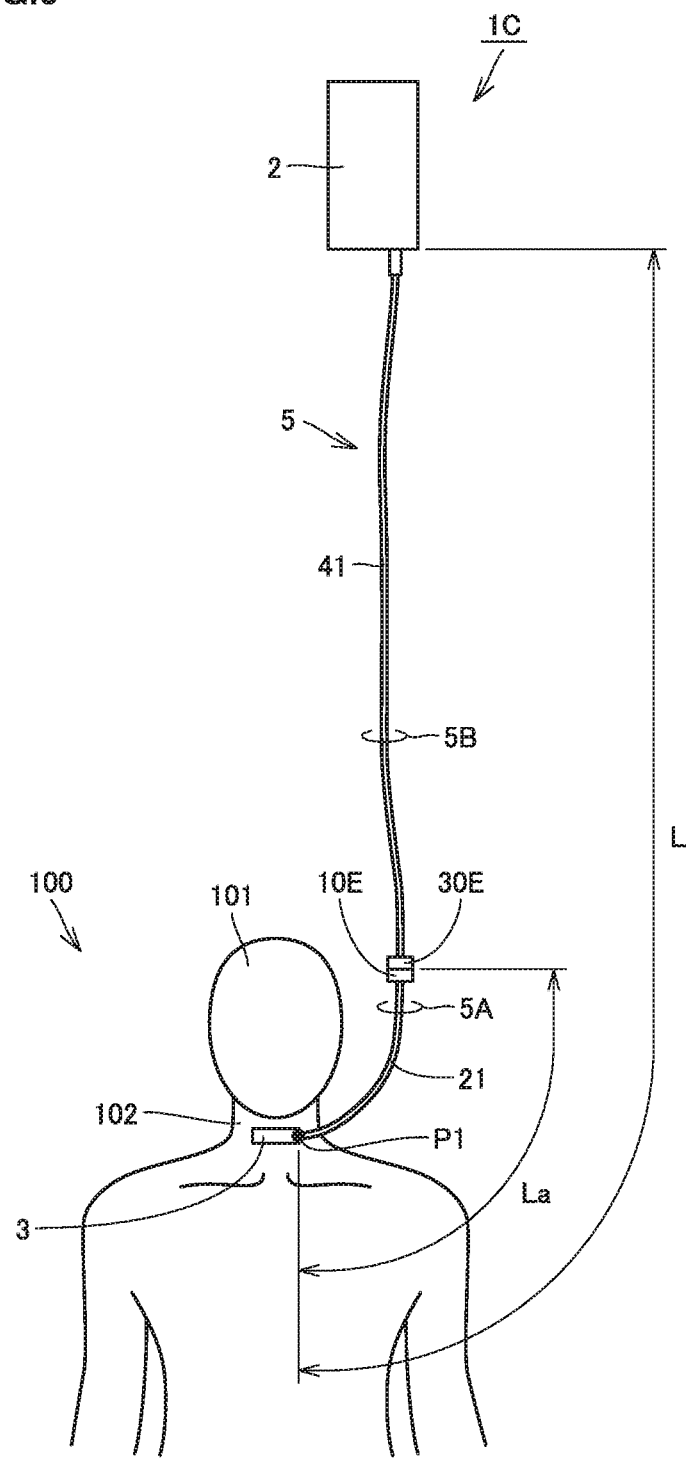
FIG. 9 is a schematic diagram showing a manner of use of a swallowing function measurement apparatus in a third preferred embodiment of the present invention.

FIG. 9 is a schematic diagram showing a manner of use of a swallowing function measurement apparatus in a third preferred embodiment of the present invention and FIG. 10 is a schematic diagram showing a construction of a living-body-side connector and an apparatus-main-body-side connector shown in FIG. 9. A swallowing function measurement apparatus 1C in the present preferred embodiment will be described below with reference to FIGS. 9 and 10.

Swallowing function measurement apparatus 1C in the present preferred embodiment is constructed to observe a motion of a neck portion and swallowing sound in a swallowing action of a subject with a piezoelectric film sensor attached to the neck portion. Therefore, as shown in FIG. 9, swallowing function measurement apparatus 1C in the present preferred embodiment is different from swallowing function measurement apparatus 1B in the second preferred embodiment described above in not including fluid-related components (see FIG. 1) such as cannula attachment portion 4, living-body-side tube 22, and apparatus-main-body-side tube 42. Swallowing function measurement apparatus 1C is able to analyze a motion of the neck portion and swallowing sound obtained as biological information as being associated with each other and thus is able to measure a swallowing function of the subject.

In this case, connection portion 5 of swallowing function measurement apparatus 1C is provided with a living-body-side connector 10E and an apparatus-main-body-side connector 30E as shown in FIG. 10. Living-body-side connector 10E and apparatus-main-body-side connector 30E are different from living-body-side connector 10A and apparatus-main-body-side connector 30A in the first preferred embodiment described above in not having first connection port 13 and second connection port 33 (see FIG. 2).

According also to this construction, by satisfying such a condition that minimum value F1 of tensile load required to disconnect living-body-side connector 10E and apparatus-main-body-side connector 30E from each other by moving living-body-side connector 10E and apparatus-main-body-side connector 30E relatively away from each other in the connected state is smaller than minimum value F2 of tensile load required to detach apparatus-main-body-side cable 41 from apparatus main body 2 by moving apparatus main body 2 and apparatus-main-body-side cable 41 relatively away from each other while apparatus-main-body-side cable 41 is connected to apparatus main body 2 (that is, F1<F2) and additionally by setting minimum value F1 of tensile load required to disconnect living-body-side connector 10E and apparatus-main-body-side connector 30E from each other to about 20 N or lower, an effect similar to the effect described in the first preferred embodiment above is able to be obtained.

In the first to third preferred embodiments and the modifications thereof of the present invention described above, an example in which any of magnetic attraction force of a magnet provided in a living-body-side connector and/or an apparatus-main-body-side connector, an adhesive force of a pressure-sensitive adhesive layer, an adhesive force of a conductive pressure-sensitive adhesive layer, or an engagement force of a locking tab and a locked portion determines holding force of the living-body-side connector and the apparatus-main-body-side connector in the connected state has been described by way of example. A recess provided in one of the living-body-side connector and the apparatus-main-body-side connector and a projection provided in the other thereof or a tip-end-side nozzle portion of a first connection port and a tip-end-side nozzle portion of a second connection port are also able to implement the engagement portion determining holding force. In this case, by appropriately adjusting a force of fitting of these components, a minimum value of tensile load required to disconnect the living-body-side connector and the apparatus-main-body-side connector from each other can appropriately be set. In this case, since it is not necessary to separately provide an engagement portion implemented by a magnet, a pressure-sensitive adhesive layer, a conductive pressure-sensitive adhesive layer, or a locking tab and a locked portion, a manufacturing cost is able to be reduced.

In the first to third preferred embodiments and the modifications thereof of the present invention described above, though an example in which the living-body-side connector is formed in a shape of a socket and the apparatus-main-body-side connector is formed in a shape of a plug has been described by way of example, naturally, the living-body-side connector can also be formed in the shape of the plug and the apparatus-main-body-side connector can also be formed in the shape of the socket.

In the first to third preferred embodiments and the modifications thereof of the present invention described above, though an example in which any of the first connection terminal and the second connection terminal includes a contact probe or at least any of the first connection terminal and the second connection terminal includes a conductive pressure-sensitive adhesive layer has been described by way of example, another construction can also naturally be adopted as the first connection terminal and the second connection terminal. Both of the connection terminals may include a contact probe, or one of the connection terminals may be in a shape of a leaf spring so as to be pressed against and contacted with the other. Alternatively, one of the connection terminals may be formed in a shape of a pin so as to be held as being sandwiched in the other connection terminal, or the connection terminals may include terminals of an insertable type including a pin and a hole.

In the first to third preferred embodiments and the modifications thereof of the present invention described above, though an example in which hermeticity is ensured simply by fitting between the first connection port and the second connection port has been described by way of example, hermeticity may be ensured by arranging a seal member such as an O ring between the connection ports.

A shape, a size, the number, and a position of placement of each portion shown in the first to third preferred embodiments and the modifications thereof of the present invention described above are by way of example, and limitation thereto is not intended. A shape or a size of the living-body-side connector and the apparatus-main-body-side connector, the number, a size, or a position of placement of the first connection terminals and the second connection terminals, a shape, a size, or a position of placement of the first connection port and the second connection port, and a shape, a size, the number, or a position of placement of a magnet, a pressure-sensitive layer, or a locking tab and a locked portion as the engagement portion are able to be modified as appropriate.

In the first to third preferred embodiments and the modifications thereof of the present invention described above, though an example in which a piezoelectric film sensor is used to obtain a motion of the neck portion or swallowing sound of a subject has been described by way of example, a potential sensor, an acceleration sensor, a pressure sensor, a magnetic sensor, or a microphone different in scheme therefrom can also naturally be used to obtain a motion of the neck portion or swallowing sound of the subject.

In the first to third preferred embodiments and the modifications thereof of the present invention described above, though an example in which a preferred embodiment of the present invention is applied to a swallowing function measurement apparatus has been described by way of example, a preferred embodiment of the present invention is applicable also to a biological information measurement apparatus other than the swallowing function measurement apparatus or a living-body-mounted apparatus other than the biological information measurement apparatus.

Characteristic features shown in the first to third preferred embodiments and the modifications thereof of preferred embodiments of the present invention described above can naturally be combined with one another within the scope not departing from the gist of the present invention.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A living-body-mounted apparatus comprising:
    an apparatus main body;
    an attachment portion including a sensor or a cannula and being attachable to any part of a living body; and
    an elongated member connecting the attachment portion and the apparatus main body to each other; wherein
    the elongated member includes a living-body-side cable including one end connected to the attachment portion, a living-body-side connector connected to the other end of the living-body-side cable, an apparatus-main-body-side cable including one end removably connected to the apparatus main body, and an apparatus-main-body-side connector connected to the other end of the apparatus-main-body-side cable;
    the living-body-side connector includes a first connection terminal electrically connected to the other end of the living-body-side cable;
    the apparatus-main-body-side connector includes a second connection terminal electrically connected to the other end of the apparatus-main-body-side cable;
    the living-body-side connector and the apparatus-main-body-side connector are capable of being in a connected state in which electrical conduction between the attachment portion and the apparatus main body is established as a result of contact between the first connection terminal and the second connection terminal owing to connection between the living-body-side connector and the apparatus-main-body-side connector and in a disconnected state in which electrical conduction between the attachment portion and the apparatus main body is cut off as a result of loss of contact between the first connection terminal and the second connection terminal owing to disconnection between the living-body-side connector and the apparatus-main-body-side connector;
    the living-body-side connector and the apparatus-main-body-side connector are provided with an engagement portion to maintain the connected state; and
    a minimum value of tensile load required to cut a connection between the living-body-side connector and the apparatus-main-body-side connector established by the engagement portion by moving the living-body-side connector and the apparatus-main-body-side connector relatively away from each other in the connected state is less than a minimum value of tensile load required to detach the apparatus-main-body-side cable from the apparatus main body by moving the apparatus main body and the apparatus-main-body-side cable relatively away from each other while the apparatus-main-body-side cable is connected to the apparatus main body.

2. The living-body-mounted apparatus according to claim 1, wherein the minimum value of tensile load required to cut the connection between the living-body-side connector and the apparatus-main-body-side connector established by the engagement portion by moving the living-body-side connector and the apparatus-main-body-side connector relatively away from each other in the connected state is equal to or lower than about 20 N.

3. The living-body-mounted apparatus according to claim 1, wherein L represents a length along a direction of extension of the elongated member from an attachment end portion position to the apparatus main body, the attachment end portion position being a position closest to a side where the apparatus main body is located, in a portion of attachment of the living-body-mounted apparatus to the living body, La represents a length along the direction of extension of the elongated member from the attachment end portion position to a position of connection between the living-body-side connector and the apparatus-main-body-side connector, and the length La is less than or equal to one half of the length L.

4. The living-body-mounted apparatus according to claim 3, wherein
    the attachment portion is attachable to any part of an upper body of a human body; and
    the length La is greater than or equal to about 30 cm and is less than or equal to about 90 cm.

5. The living-body-mounted apparatus according to claim 1, wherein the engagement portion includes a magnet.

6. The living-body-mounted apparatus according to claim 1, wherein the engagement portion includes a locking tab provided in one of the living-body-side connector and the apparatus-main-body-side connector and a locked portion provided in the other of the living-body-side connector and the apparatus-main-body-side connector and locked by the locking tab.

7. The living-body-mounted apparatus according to claim 1, wherein at least one of the first connection terminal and the second connection terminal includes a contact probe.

8. The living-body-mounted apparatus according to claim 1, wherein
    the living-body-mounted apparatus is a biological information measurement apparatus that measures biological information;
    the attachment portion includes the sensor which converts biological information into an electric signal.

9. The living-body-mounted apparatus according to claim 8, wherein the living-body-mounted apparatus is a swallowing function measurement apparatus that measures a swallowing function.

10. The living-body-mounted apparatus according to claim 9, wherein the attachment portion includes the sensor, and the sensor is a piezoelectric film sensor attachable to a neck portion of the living body.

11. A living-body-mounted apparatus comprising:
an apparatus main body;
an electric-related attachment portion including a sensor and being attachable to any part of a living body;
a fluid-related attachment portion including a cannula and being attachable to any part of the living body; and
an elongated member connecting the electric-related attachment portion and the fluid-related attachment portion to the apparatus main body; wherein
the elongated member includes a living-body-side cable including one end connected to the electric-related attachment portion, a living-body-side tube includes one end connected to the fluid-related attachment portion, a living-body-side connector connected to the other end of the living-body-side cable and the other end of the living-body-side tube, an apparatus-main-body-side cable includes one end removably connected to the apparatus main body, an apparatus-main-body-side tube includes one end removably connected to the apparatus main body, and an apparatus-main-body-side connector connected to the other end of the apparatus-main-body-side cable and the other end of the apparatus-main-body-side tube;
the living-body-side connector includes a first connection terminal electrically connected to the other end of the living-body-side cable and a first connection port communicating with the other end of the living-body-side tube;
the apparatus-main-body-side connector includes a second connection terminal electrically connected to the other end of the apparatus-main-body-side cable and a second connection port communicating with the other end of the apparatus-main-body-side tube;
the living-body-side connector and the apparatus-main-body-side connector are capable of being in a connected state in which electrical conduction between the electric-related attachment portion and the apparatus main body is established as a result of contact between the first connection terminal and the second connection terminal owing to connection between the living-body-side connector and the apparatus-main-body-side connector and communication between the fluid-related attachment portion and the apparatus main body is established as a result of fitting between the first connection port and the second connection port and in a disconnected state in which electrical conduction between the electric-related attachment portion and the apparatus main body is cut off as a result of loss of contact between the first connection terminal and the second connection terminal owing to disconnection between the living-body-side connector and the apparatus-main-body-side connector and communication between the fluid-related attachment portion and the apparatus main body is cut off as a result of absence of fitting between the first connection port and the second connection port;
the living-body-side connector and the apparatus-main-body-side connector are provided with an engagement portion to maintain the connected state; and
a minimum value of tensile load required to cut a connection between the living-body-side connector and the apparatus-main-body-side connector established by the engagement portion by moving the living-body-side connector and the apparatus-main-body-side connector relatively away from each other in the connected state is less than a minimum value of tensile load required to detach the apparatus-main-body-side cable and the apparatus-main-body-side tube from the apparatus main body by moving the apparatus-main-body-side cable and the apparatus-main-body-side tube relatively away from the apparatus main body while the apparatus-main-body-side cable and the apparatus-main-body-side tube are connected to the apparatus main body.

12. The living-body-mounted apparatus according to claim 11, wherein a filtration filter is removably assembled to at least one of the first connection port and the second connection port.

13. The living-body-mounted apparatus according to claim 11, wherein the minimum value of tensile load required to cut the connection between the living-body-side connector and the apparatus-main-body-side connector established by the engagement portion by moving the living-body-side connector and the apparatus-main-body-side connector relatively away from each other in the connected state is equal to or lower than about 20 N.

14. The living-body-mounted apparatus according to claim 11, wherein L represents a length along a direction of extension of the elongated member from an attachment end portion position to the apparatus main body, the attachment end portion position being a position closest to a side where the apparatus main body is located, in a portion of attachment of the living-body-mounted apparatus to the living body, La represents a length along the direction of extension of the elongated member from the attachment end portion position to a position of connection between the living-body-side connector and the apparatus-main-body-side connector, and the length La is less than or equal to one half of the length L.

15. The living-body-mounted apparatus according to claim 14, wherein
the electric-related attachment portion is attachable to any part of an upper body of a human body; and
the length La is greater than or equal to about 30 cm and is less than or equal to about 90 cm.

16. The living-body-mounted apparatus according to claim 11, wherein the engagement portion includes a magnet.

17. The living-body-mounted apparatus according to claim 11, wherein at least one of the first connection terminal and the second connection terminal includes a contact probe.

18. The living-body-mounted apparatus according to claim 11, wherein
the living-body-mounted apparatus is a biological information measurement apparatus that measures biological information; and
the sensor of the electric-related attachment portion converts biological information into an electric signal.

19. The living-body-mounted apparatus according to claim 18, wherein the living-body-mounted apparatus is a swallowing function measurement apparatus that measures a swallowing function.

20. The living-body-mounted apparatus according to claim 19, wherein the sensor of the electric-related attachment portion is a piezoelectric film sensor attachable to a neck portion of the living body.

* * * * *